(12) United States Patent
Jeong

(10) Patent No.: US 9,492,685 B2
(45) Date of Patent: Nov. 15, 2016

(54) METHOD AND APPARATUS FOR CONTROLLING AND MONITORING POSITION OF RADIATION TREATMENT SYSTEM

(71) Applicant: Infinitt Healthcare Co., Ltd., Seoul (KR)

(72) Inventor: Jae Won Jeong, Seoul (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 69 days.

(21) Appl. No.: 14/333,291

(22) Filed: Jul. 16, 2014

(65) Prior Publication Data

US 2015/0360054 A1 Dec. 17, 2015

(30) Foreign Application Priority Data

Jun. 13, 2014 (KR) .................. 10-2014-0072007
Jun. 19, 2014 (KR) .................. 10-2014-0074737

(51) Int. Cl.
*A61N 5/10* (2006.01)

(52) U.S. Cl.
CPC ........... *A61N 5/1049* (2013.01); *A61N 5/1069* (2013.01); *A61N 2005/1059* (2013.01); *A61N 2005/1074* (2013.01)

(58) Field of Classification Search
CPC ...... A61N 5/10; A61N 5/103; A61N 5/1048; A61N 5/1049; A61N 2005/1051; A61N 2005/1059; A61N 2005/1061; A61N 2005/1056; A61B 6/0457
USPC .................. 378/65, 68, 163, 165, 166, 205
See application file for complete search history.

(56) References Cited

U.S. PATENT DOCUMENTS

| 7,199,382 | B2 | 4/2007 | Rigney et al. |
| 7,343,189 | B2* | 3/2008 | Kagermeier ............. A61B 6/08 378/20 |
| 7,438,685 | B2 | 10/2008 | Burdette et al. |
| 7,574,251 | B2 | 8/2009 | Lu et al. |
| 7,587,024 | B2 | 9/2009 | Grozinger et al. |
| 7,639,854 | B2 | 12/2009 | Schnarr et al. |
| 7,860,550 | B2 | 12/2010 | Saracen et al. |
| 8,160,205 | B2 | 4/2012 | Saracen et al. |

(Continued)

FOREIGN PATENT DOCUMENTS

| KR | 10-0740341 B1 | 7/2007 |
| KR | 10-2008-0039916 A | 5/2008 |

(Continued)

*Primary Examiner* — Jurie Yun
(74) *Attorney, Agent, or Firm* — Mintz Levin Cohn Ferris Glovsky and Popeo, P.C.; Kongsik Kim; Jonathon Western

(57) ABSTRACT

Disclosed are a method and apparatus for controlling and monitoring a position of a radiation treatment system, the method of controlling the position of the radiation treatment system, including: capturing a first image of a patient on a first axis and a second axis using a first camera and capturing a second image of the patient on the second axis and a third axis using a second camera; acquiring a third image of the patient captured using the first camera and a fourth image of the patient captured using the second camera during previous radiation treatment; and controlling a position of the patient to compensate for the calculated first position change based on the first image and the third image and the calculated second position change based on the second image and the fourth image.

16 Claims, 11 Drawing Sheets

(56) References Cited

U.S. PATENT DOCUMENTS

| | | |
|---|---|---|
| 8,229,068 B2 | 7/2012 | Lu et al. |
| 8,269,195 B2 | 9/2012 | Rigney et al. |
| 8,280,136 B2 * | 10/2012 | Gotardo ............... G06K 9/6207 378/4 |
| 8,457,279 B2 | 6/2013 | Saracen et al. |
| 8,745,789 B2 | 6/2014 | Saracen et al. |
| 2003/0206614 A1 | 11/2003 | Kendrick et al. |
| 2011/0249088 A1 | 10/2011 | Hannibal et al. |
| 2013/0085387 A1 | 4/2013 | Chen et al. |
| 2014/0037173 A1 | 2/2014 | Gum et al. |

FOREIGN PATENT DOCUMENTS

| | | |
|---|---|---|
| KR | 10-1070216 B1 | 10/2011 |
| KR | 10-1212792 B1 | 12/2012 |
| KR | 10-1249815 B1 | 4/2013 |

* cited by examiner

FROM S130

↓

CALCULATE THE NUMBER OF PIXELS IN LENGTH OF DIAGNOSIS COUCH AND THE NUMBER OF PIXELS IN POSITION OF PATIENT FROM THIRD IMAGE ~S210

↓

CALCULATE THE NUMBER OF PIXELS IN LENGTH OF DIAGNOSIS COUCH AND THE NUMBER OF PIXELS IN POSITION OF PATIENT FROM FIRST IMAGE ~S220

↓

CALCULATE POSITION CHANGE OF PATIENT USING CALCULATED NUMBER OF PIXELS ~S230

↓

TO S150

METHOD AND APPARATUS FOR CONTROLLING AND MONITORING POSITION OF RADIATION TREATMENT SYSTEM

CROSS-REFERENCE TO RELATED APPLICATION

This application claims under 35 U.S.C. §119(a) the benefit of Korean Applications No. 10-2014-0072007 filed on Jun. 13, 2014, and No. 10-2014-0074737 filed on Jun. 19, 2014, which applications are incorporated herein by reference.

TECHNICAL FIELD

The present invention relates to controlling and monitoring a position of a radiation treatment system, and more particularly, to a method and apparatus for controlling and monitoring a position of a radiation treatment system, whereby a radiation dose exposed to a patient can be reduced, a position of the patient can be automatically controlled during radiation treatment and even when the patient moves during radiation treatment, the position of the patient can be controlled through monitoring so that treatment beams can be radiated onto a region of interest (ROI).

BACKGROUND ART

In general, many systems or apparatuses need to be used for radiation treatment in hospitals. Types of these systems and apparatuses include an electronic medical record (EMR) system, an order communication system (OCS), a picture archiving and communication system (PACS), a radiation treatment planning (RTP) system, and a radiation treatment device, for example, a linear accelerator (LINAC).

OCS is a system that transmits a database (DB) for storing various medical information and patient examination data and prescriptions that are made after doctors have diagnosed patients, to corresponding examination departments over a communication network.

The EMR system is a system that is configured to store and search for EMR.

PACS is a system that stores and transmits images captured by at least one medical imaging apparatus including a computed tomography (CT) device, a magnetic resonance imaging (MRI) device, a positron emission tomography (PET) device, a CT simulator, and computed radiography (CR), in a computer file format. PACS is equipment that has been mostly introduced in medium-sized hospitals.

The RTP system is a system that systematically establishes (draws up) a patient's radiation treatment plan, i.e., drawing-up of radiation treatment plan information, calculating and checking a radiation dose. By using the RTP system, a user selects an optimum image from among images of the patient's body in areas where cancer is located, which are acquired by the CT device or the MRI device; or a doctor examines the patient's medical photos, digitizes and images them and then performs basic image processing, sets reference coordinates of the acquired images and performs contouring of each of the areas thereby calculating a direction of beams and a radiation dose according to the sizes of the areas in which cancer has occurred.

A basic principle of radiation treatment is to target the treatment to minimize the occurrence of acute and chronic radiation reactions that may occur in normal tissues, reduce complications, or prevent causing a secondary tumor while performing cancer treatment. To this end, an appropriate radiation treatment plan needs to be established.

The radiation treatment device is a device that actually performs radiation treatment on the patient based on the radiation treatment plan that is drawn-up using the RTP system.

Cancer treatment methods in the area of radiation oncology have developed over the years and have become diverse. Thus, new treatment devices and applications of various treatment methods have been developed.

A procedure of performing radiation treatment on the patient in a radiation oncology department will be described below. First, the patient's medical images are acquired using a medical imaging device so as to acquire information regarding the patient's cancer. Thereafter, the radiation treatment plan is established based on the patient's medical images using the RTP system. Next, radiation treatment is performed using the radiation treatment device based on the radiation treatment plan that is established using the RTP system.

In this case, radiation treatment devices, such as LINAC, brachytherapy, cyberknife, and tomotherapy, have been developed and used. These radiation treatment devices have been properly selected according to the patient's cancer state or treatment area.

In a conventional radiation treatment system, before radiation treatment is performed, radioactive rays have been used so as to check whether the patient position during present radiation treatment is same as his or her position during previous radiation treatment, for example, during initial radiation treatment or during simulation treatment.

For example, since, in tomotherapy, treatment beams are radiated while diagnosis radiographs are taken, irradiation for checking the patient's initial position while irradiation is performed in a double manner, may cause problems in the treatment plan.

Also, even though a difference between the patient's original position and the patient's current position is known, when images are matched or fused so that the patient can be moved or a diagnosis couch is manually moved, the patient may move, and treatment may be delayed, which causes inconvenience during the radiation treatment.

Furthermore, in the conventional radiation treatment system, when the patient's movement occurs during radiation treatment, the treatment beams are radiated onto a position or region different from a region of interest (ROI) of radiation treatment. Thus, cancer cells in the ROI are not treated but normal tissues are exposed to radiation and may be negatively affected.

Thus, it is essential to perform radiation treatment by continuously monitoring the patient's movement.

Korean Patent Registration No. 10-1212792 that is a prior art for solving these problems discloses a patient arrangement system for a radiation therapy system, whereby control signals for moving at least one of a movable patient positioner and a radiation nozzle are generated and position information that indicate current spatial positions of one or more selected from the patient positioner, the radiation nozzle, and fixed reference objects are obtained from a plurality of external measurement devices.

However, the prior art has problems that, since the plurality of external measurement devices are disposed at several angles and the patient position is checked and corrected using image analysis and position signals from each of the plurality of external measurement devices, the structure of the patient arrangement system is complicated and the amount of calculation is increased.

Korean Patent Publication No. 2008-0039916 that is a prior art for monitoring a patient position or movement in a conventional radiation treatment system, discloses a system and method of performing radiation treatment in a moving ROI, whereby the patient is monitored while radiation treatment is performed and a treatment plan is changed in consideration of breathing patterns determined in a monitoring operation.

However, in the prior art, since all of treatment plans need to be set based on the patient's breathing patterns, when the patient's breathing patterns are different from set breathing patterns, it is difficult to change the treatment plans. In addition, since only the breathing patterns are considered, if the patient moves while on the diagnosis couch in a state in which the same breathing patterns are maintained, treatment beams may not be radiated onto the ROI but may be radiated onto a different region such that a normal part may be exposed to the treatment beams.

Thus, there is an increasing need for a method of automatically controlling a patient position, whereby the patient position can be automatically controlled with a simple structure while reducing a radiation dose exposed to the patient and the patient position is monitored so that, even when the patient moves, a normal part can be prevented from being exposed to treatment beams.

SUMMARY OF THE DISCLOSURE

Accordingly, the present invention has been made keeping in mind the above problems occurring in the prior art, and an object of the present invention is to provide a method and apparatus for controlling and monitoring a position of a radiation treatment system, whereby a radiation dose exposed to a patient can be reduced and a position of the patient can be automatically controlled during radiation treatment.

Another object of the present invention is to provide a method and apparatus for controlling and monitoring a position of a radiation treatment system, whereby a position of a patient can be automatically controlled by comparing images of the patient position during previous radiation treatment with images of the patient position during current radiation treatment using two fixed cameras.

Another object of the present invention is to provide a method and apparatus for controlling and monitoring a position of a radiation treatment system, whereby the number of pixels per unit length is calculated and a position of a patient can be automatically controlled using the calculated number of pixels.

Another object of the present invention is to provide a method and apparatus for controlling and monitoring a position of a radiation treatment system, whereby, even when patient's movement occurs during radiation treatment, a position of the patient can be controlled so that treatment beams can be radiated onto a region of interest (ROI).

Another object of the present invention is to provide a method and apparatus for controlling and monitoring a position of a radiation treatment system, whereby a patient's movement is monitored by comparing images of the patient position during previous radiation treatment with images of the patient position during current radiation treatment using two fixed cameras and whether to control radiation treatment beams is controlled through monitoring so that non-target areas can be prevented from being exposed to radiation treatment beams.

In accordance with an aspect of the present invention, there is provided a method of controlling a position of a radiation treatment system, including: capturing a first image of a patient on a first axis and a second axis using a first camera and capturing a second image of the patient on the second axis and a third axis using a second camera; acquiring a third image of the patient captured using the first camera and a fourth image of the patient captured using the second camera during previous radiation treatment; calculating a first position change of the patient on the first axis and the second axis using the first image and the third image and calculating a second position change of the patient on the second axis and the third axis using the second image and the fourth image; and controlling a position of the patient to compensate for the calculated first position change and the calculated second position change so that the position of the patient is identical to a position of the patient during previous radiation treatment.

The calculating of the first position change of the patient and the second position change of the patient may include calculating the first position change and the second position change using at least one selected from the group consisting of at least one reference pattern that is previously formed on a diagnosis couch on which the patient lies, at least one feature point that is marked on the patient, and the patient's shape.

The calculating of the first position change of the patient and the second position change of the patient may include calculating a first number of pixels on a length of the diagnosis couch on which the patient lies, and a second number of pixels on the position of the patient within the diagnosis couch from the third image and the fourth image, calculating a third number of pixels on the length of the diagnosis couch and a fourth number of pixels on the position of the patient within the diagnosis couch from the first image and the second image, and calculating the first position change and the second position change using the calculated first to fourth numbers of pixels.

The controlling of the position of the patient may include controlling the position of the patient by moving or rotating the diagnosis couch on which the patient lies, in directions of the first axis, the second axis, and the third axis using the first position change and the second position change.

In accordance with another aspect of the present invention, there is provided an apparatus for controlling a position of a radiation treatment system, including: a first camera that captures an image of a patient on a first axis and a second axis of a diagnosis couch; a second camera that captures an image of the patient on the second axis and a third axis; an image acquisition unit that acquires a first image and a second image of the diagnosis couch and the patient that were previously captured and stored by the first camera and the second camera during previous radiation treatment; and a position change calculation unit that receives a third image and a fourth image that are captured by the first camera and the second camera for current radiation treatment, calculates a first position change of the patient on the first axis and the second axis using the first image and the third image and calculates a second position change of the patient on the second axis and the third axis using the second image and the fourth image; and a patient position controller that controls a position of the patient using the calculated first position change and the calculated second position change so that the position of the patient is identical to a position of the patient during previous radiation treatment.

In accordance with another aspect of the present invention, there is provided a method of monitoring a position of a radiation treatment system, including: capturing a first image of a patient on a first axis and a second axis using a first camera and capturing a second image of the patient on the second axis and a third axis using a second camera during radiation treatment; acquiring a third image of the patient captured using the first camera and a fourth image of the patient captured using the second camera during previous radiation treatment; calculating a first correlation value between the first image and the third image by comparing the first image with the third image and calculating a second correlation value between the second image and the fourth image by comparing the second image with the fourth image; and determining whether the first correlation value and the second correlation value are within a predetermined threshold value range, and if it is determined that the first correlation value and the second correlation value are out of the predetermined threshold value range, determining that the position of the patient is out of a radiation treatment position, and controlling treatment beams so that radiation of the treatment beams is stopped.

The method may further include: controlling a diagnosis couch on which the patient lies, so that the patient is in the desired radiation treatment position; and if the position of the patient is the desired radiation treatment position, controlling the treatment beams so that the treatment beams can be radiated.

The acquiring of the third image of the patient and the fourth image of the patient may include acquiring a third deformation image and a fourth deformation image that are generated by deforming the third image and the fourth image through normalization, segmentation, and edge detection, and the calculating of the first correlation value and the second correlation value may include, after acquiring a first deformation image and a second deformation image that are generated by deforming the first image and the second image through normalization, segmentation, and edge detection, calculating the first correlation value by comparing the first deformation image with the third deformation image and calculating the second correlation value by comparing the second deformation image with the fourth deformation image.

The method may further include: determining whether correction of an angle and position of at least one of the first camera and the second camera by comparing the first image and the second image with reference images corresponding to the first image and the second image; and as a result of determination, if correction is required, calculating a correction value of the angle and position of at least one of the first camera and the second camera, wherein the calculating of the second correlation value comprises calculating the first correlation value and the second correlation value by reflecting the calculated correction value.

In accordance with another aspect of the present invention, there is provided an apparatus for monitoring a position of a radiation treatment system, including: a first camera that captures an image of a patient on a first axis and a second axis at a diagnosis couch; a second camera that captures an image of the patient on the second axis and a third axis; an image acquisition unit that acquires a first image and a second image of the diagnosis couch and the patient that were previously captured and stored by the first camera and the second camera during previous radiation treatment; a correlation value calculation unit that receives a third image and a fourth image that are captured by the first camera and the second camera during current radiation treatment, calculates a first correlation value between the first image and the third image by comparing the first image with the third image and calculates a second correlation value between the second image and the fourth image by comparing the second image with the fourth image; and a monitoring controller that determines whether the first correlation value and the second correlation value are within a predetermined threshold value range, and if it is determined that the first correlation value and the second correlation value are out of the predetermined threshold value range, determines that the patient is out of a desired radiation treatment position, controls the treatment beams so that radiation of the treatment beams is stopped.

BRIEF DESCRIPTION OF THE DRAWINGS

The above and other objects, features and advantages of the present invention will be more clearly understood from the following detailed description taken in conjunction with the accompanying drawings, in which:

FIG. 2 is a flowchart illustrating Operation S140 illustrated in FIG. 1, in accordance with an embodiment of the present invention;

DETAILED DESCRIPTION OF THE DISCLOSURE

Figure 1:
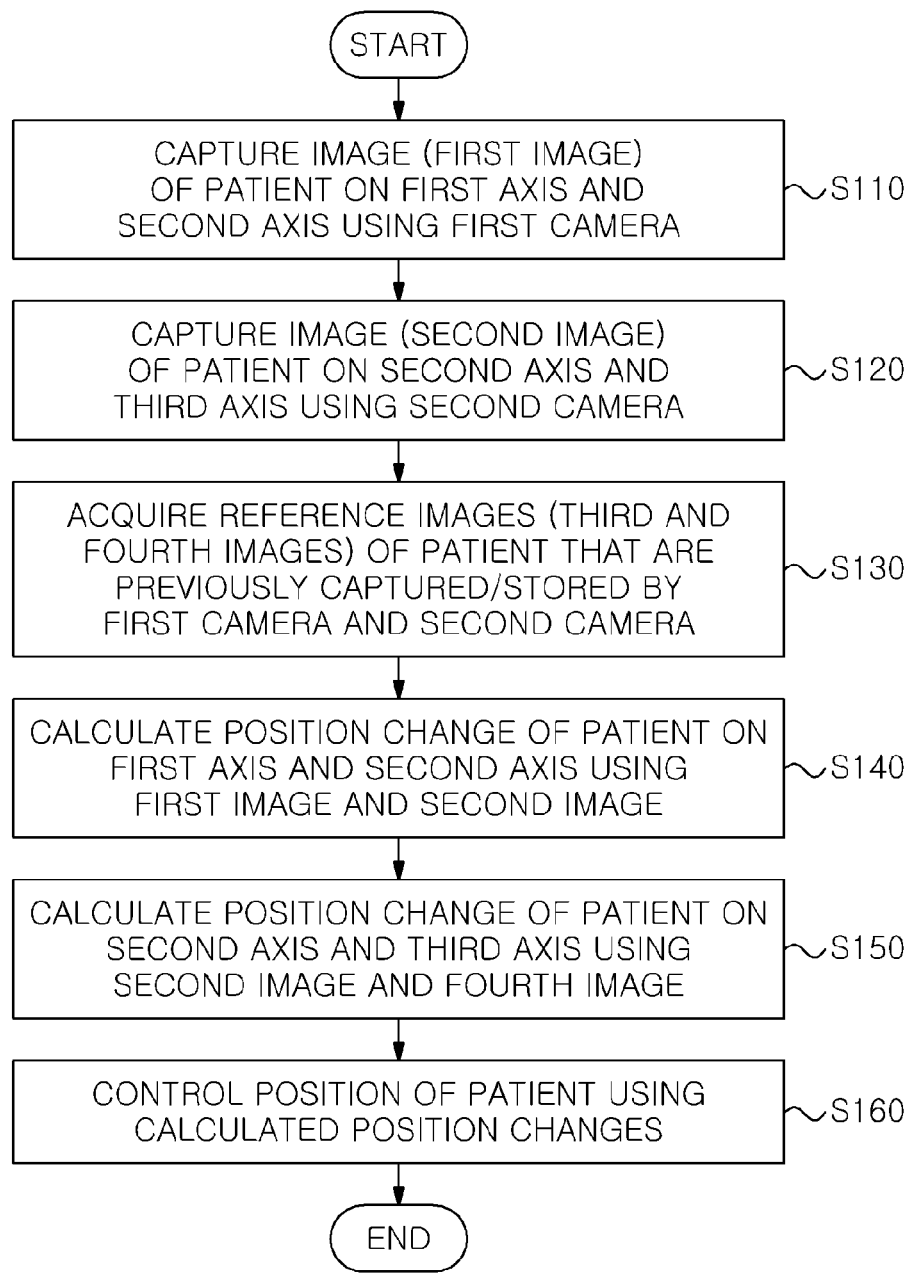
FIG. 1 is a flowchart illustrating a method of controlling a position of a radiation treatment system in accordance with an embodiment of the present invention.

Hereinafter, embodiments of the present invention will be described in detail with reference to the accompanying drawings. Reference now should be made to the elements of drawings, in which the same reference numerals are used throughout the different drawings to designate the same elements. In the following description, detailed descriptions of known elements or functions that may unnecessarily make the gist of the present invention obscure will be omitted.

Hereinafter, a method and apparatus for controlling and monitoring a position of a radiation treatment system in accordance with embodiments of the present invention will be described in detail with reference to FIGS. 1 to 11.

The present invention is to automatically control a patient position on a diagnosis couch of the radiation treatment system, i.e., to control the patient position during current radiation treatment so that the position is identical a position held during previous radiation treatment by comparing an image of the patient position during previous radiation treatment with an image of the patient position during current radiation treatment using a camera that captures an image at an upper portion of the diagnosis couch and a camera that captures an image at sides of the diagnosis couch, so that a radiation dose exposed to the patient can be reduced and the patient position can be automatically controlled with a simple structure.

In addition, the present invention is to monitor the patient position during radiation treatment, i.e., to automatically monitor the patient's movement using a correlation value obtained by comparing images captured by the camera disposed at the upper portion of the diagnosis couch and the camera disposed at sides of the diagnosis couch with reference images so that treatment beams can be prevented from being radiated onto a normal part and the patient position can be automatically controlled so that the reliability of radiation treatment can be improved.

FIG. 1 is a flowchart illustrating a method of controlling a position of a radiation treatment system in accordance with an embodiment of the present invention. The method of controlling the position of the radiation treatment system illustrated in FIG. 1 may be executed by a processor of a computing system that may control the position of the radiation treatment system and may be stored in the form of instructions loaded into memory connected to the processor.

Referring to FIG. 1, the method according to the present invention includes capturing an image of a patient on a first axis and a second axis of a diagnosis couch (hereinafter, referred to as a "first image") using a first camera disposed at the radiation treatment system and capturing an image of the patient on the second axis and a third axis of the diagnosis couch (hereinafter, referred to as a "second image") using a second camera disposed at the radiation treatment system (Operations S110 and S120).

Figure 4:
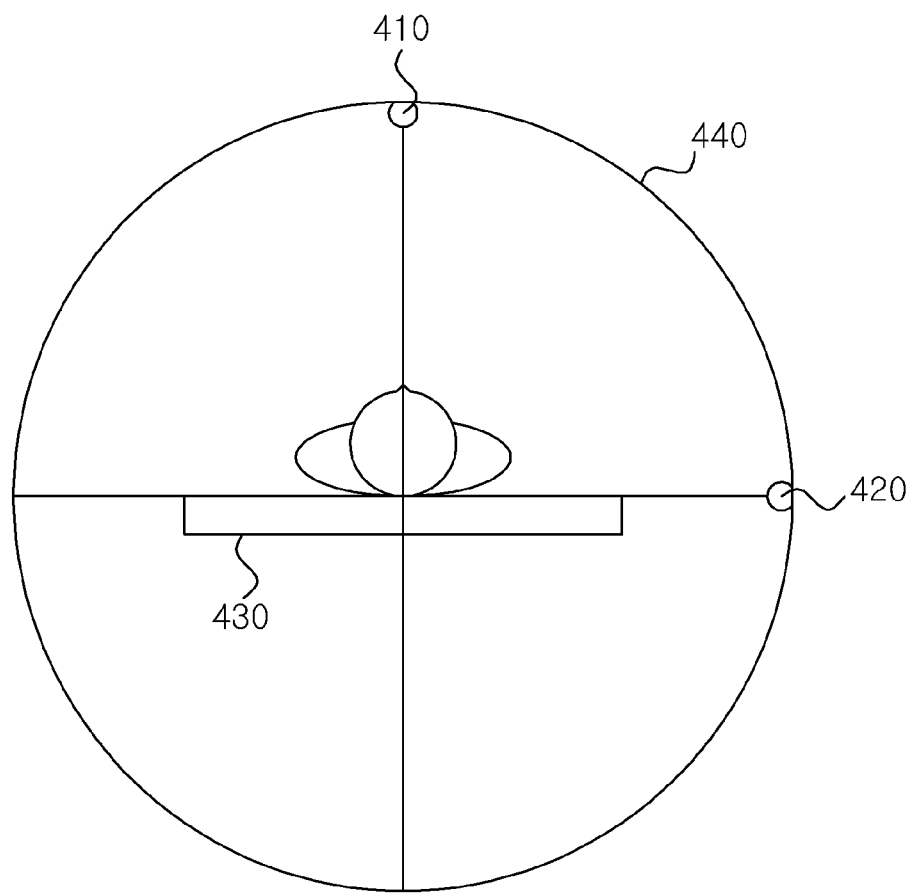
FIG. 4 is a diagram illustrating an example of a radiation treatment system for describing the present invention.

In this case, a first camera 410 may be a camera that captures an image of the patient at an upper portion of a diagnosis couch 430, and a second camera 420 may be a camera that captures an image of the patient at sides of the diagnosis couch 430, as illustrated in FIG. 4, and the first axis, the second axis, and the third axis may be an x-axis, a y-axis, and a z-axis, respectively. The first camera and the second camera may be disposed to be fixed to a gantry 440 of the radiation treatment system but may be disposed to be fixed at a different particular position instead of the gantry 440.

A camera according to the present invention is a photographing device using a charge coupled device (CCD) and a complementary metal-oxide semiconductor (CMOS).

Thus, the first image captured by the first camera 410 may be an image for mainly detecting a position change of the patient on the x-axis and the y-axis, and the second image captured by the second camera 420 may be an image for mainly detecting a position change of the patient on the y-axis and the z-axis.

The first image and the second image according to the present invention may be an upper image and a lateral image for checking the patient position during current radiation treatment.

When the first image and the second image are captured, reference images of the patient that were previously captured and stored by the first camera 410 and the second camera 420 during previous radiation treatment are acquired (Operation S130).

In this case, the reference images are medical images including the images captured by the first camera 410 and the second camera 420 during previous radiation treatment, for example, during initial radiation treatment. In the present invention, the reference images will be referred to as a third image and a fourth image.

That is, the third image is an image of the patient on the x-axis and the y-axis captured by the first camera 410 during previous radiation treatment in which radiation treatment has been performed, and the fourth image is an image of the patient on the y-axis and the z-axis captured by the second camera 420 during previous radiation treatment.

The third image and the fourth image may be acquired from a separate storage device or system connected to the radiation treatment system, for example, a picture archiving and communication system (PACS), using the patient's information. Of course, the method according to the present invention may be performed when a user's input for controlling the patient position by a medical specialist who performs radiation treatment is received via a user interface.

If the third image and the fourth image of the patient position during previous radiation treatment are acquired in Operation S130, a position change of the patient on the first axis and the second axis (hereinafter, referred to as a "first position change") is calculated using the third image and the first image corresponding to the third image, and a position change of the patient on the second axis and the third axis (hereinafter, referred to as a "second position change") is calculated using the fourth image and the second image corresponding to the fourth image (Operations S140 and S150). In this case, the position changes may be calculated based on positions of markers indicated on the patient's body and a particular reference position of a previously-checked diagnosis couch 430. According to the present invention, all changes in positions of the patient on the diagnosis couch 430 and all changes in poses of the patient may be calculated.

The present invention is a technique for moving the diagnosis couch on which the patient lies, so that a region of interest (ROI) of radiation treatment can be correctly positioned in the path of radioactive rays and thus radiation treatment in a current state can achieve a predetermined objective, by calculating a difference between the position and the pose of the patient during previous radiation treatment and the current position and the current pose of the patient.

The patient may have moved in x-axis and y-axis directions from the diagnosis couch 430 compared to previous treatment or may be lying obliquely compared to former treatment. Alternatively, the patient's pose may be slightly twisted compared to previous treatment. According to the present invention, a position change of the patient in an x-y plane and rotation on the x-y plane may be extracted by comparing the first image with the third image using a plurality of markers indicated on the patient's body. Also, when the patient's pose is a supine pose, a prone pose, or a lateral pose, a difference between the supine pose, the prone pose, or the lateral pose and a further-twisted pose of the patient compared to previous treatment may also be detected.

For example, if, in the lateral pose, positions of the plurality of markers in the first image and the third image in the y-axis direction are the same and positions of the plurality of markers are different only in the x-axis direction, it may be detected that an angle at which the patient is lying in the lateral direction, has been changed.

Here, according to the present invention, by analyzing a change in pixels between particular reference positions of the diagnosis couch 430, even though positions of the diagnosis couch 430 are the same, it may be checked whether the position or pose of the patient has been changed or the diagnosis couch 430 itself has been moved.

In the present invention, a position change of the patient can be calculated using the number of pixels in greater detail. This will be described below with reference to FIG. 2.

FIG. 2 is a flowchart illustrating Operation S140 illustrated in FIG. 1, in accordance with an embodiment of the present invention.

Referring to FIG. 2, Operation S140 of calculating the first position change includes calculating the number of pixels in a predetermined length of the diagnosis couch 430, for example, a width or length of the diagnosis couch 430, and the number of pixels in the patient position from the third image that is the reference image (Operation S210).

That is, in Operation S210, the number of pixels (pixel/mm) per unit length of the diagnosis couch 430 and the number of pixels in the patient position on the diagnosis couch 430 are calculated. For example, in Operation S210, the number of pixels in the width of the diagnosis couch 430 and the number of pixels per unit length may be calculated from the third image using the predetermined width of the diagnosis couch 430, and the number of pixels in positions of the patient in the x-axis and y-axis directions of the diagnosis couch 430 may be calculated based on an end of the diagnosis couch 430 or based on at least one reference pattern or reference mark that is pre-set in the diagnosis couch 430. Of course, the patient position in the x-axis and y-axis directions on the diagnosis couch 430 may be calculated using the number of pixels per unit length calculated based on at least one reference pattern that is pre-set in the diagnosis couch 430 and feature points that are pre-set on the patient, i.e., markers indicated on the eyes, nose, mouth, or elsewhere on the patient, and the x-axis position and the y-axis position of the patient at the diagnosis couch 430 may be calculated using the reference pattern, the patient's shape, body length, and the number of pixels per unit length of lengths of a distance between body parts.

Similarly, in order to check the patient position on the diagnosis couch 430 for current radiation treatment, the number of pixels in the width or length of the diagnosis couch 430 and the number of pixels in the patient position are calculated from the first image (Operation S220).

That is, if the number of pixels in the width of the diagnosis couch 430 is calculated in Operation S220, a position change on the first axis, the second axis, and the third axis of the first image may be known using the number of pixels per unit length calculated in Operation S210. For example, if the number of pixels per unit length in Operation S210 and the number of pixels per unit length in Operation S220 are equal to 3, it may be determined that no position change on the z-axis has occurred, and if the number of pixels per unit length in Operation S210 and the number of pixels per unit length in Operation S220 are different from each other, it may be determined that a position change on the z-axis has occurred. Of course, if the number of pixels per unit length in Operation S210 and the number of pixels per unit length in Operation S220 are the same and the number of pixels from four sides of an image to the diagnosis couch 430 and the number of pixels in the patient position at the diagnosis couch 430 are different from each other, it may be determined that the diagnosis couch 430 or the patient position has changed in the x-axis and y-axis directions. On the other hand, if the number of pixels per unit length in the first image and the number of pixels per unit length in the third image are different from each other, a position change of the diagnosis couch 430 has occurred in the z-axis direction so that a position change of the patient on the diagnosis couch 430 in the x-axis and y-axis directions may be calculated by reflecting the position change on the z-axis.

Figure 5:
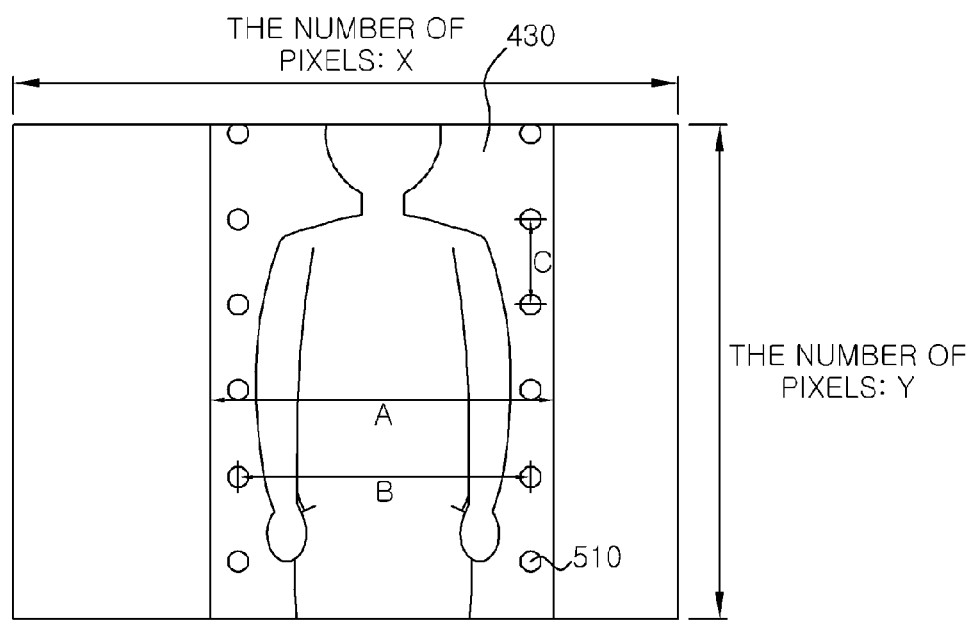
FIG. 5 is a diagram illustrating an example of an image captured by a first camera.

The number of pixels per unit length in Operation S210 and the number of pixels per unit length in Operation S220 may also be calculated using distances B and C between reference patterns 510 in addition to using a width A and a length of the diagnosis couch 430, as illustrated in FIG. 5.

Figure 6:
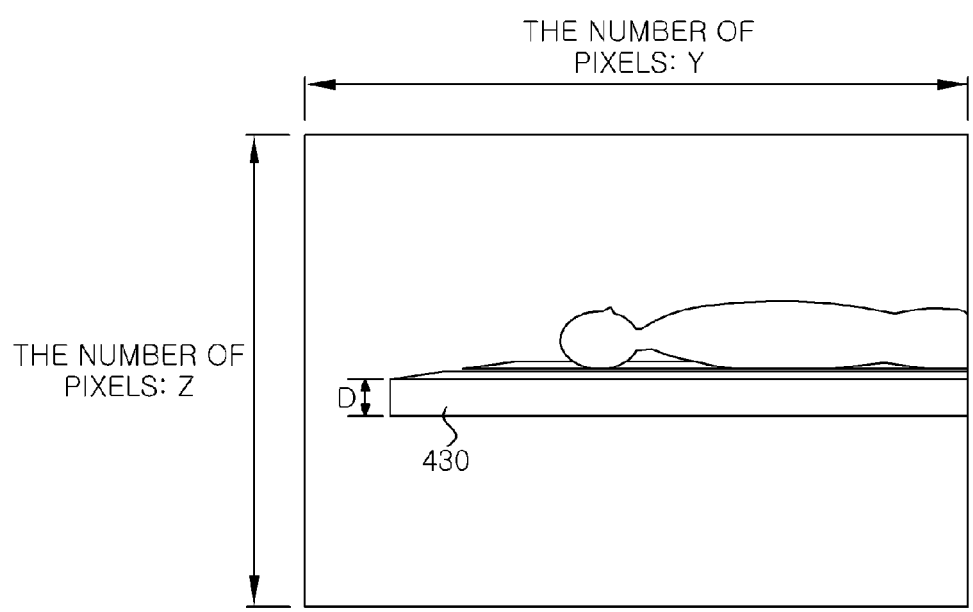
FIG. 6 is a diagram illustrating an example of an image captured by a second camera.

Similarly, the number of pixels per unit length in the second image and the number of pixels per unit length in the fourth image may be calculated using a height D of the diagnosis couch 430, as illustrated in FIG. 6.

If the numbers of pixels are calculated in Operations S210 and S220 in this way, a position change of the patient is calculated using the calculated number of pixels or the calculated number of pixels per unit length (Operation S230).

Although, in FIG. 1, the position change of the patient in the x-axis and y-axis directions is calculated using the first image and the third image, a position change of the patient in the z-axis direction may also be calculated in addition to the x-axis and y-axis directions.

An operation of calculating the position change of the patient using the first image and the third image described in FIG. 2 may be applied to an operation of calculating a position change of the patient using the second image and the fourth image. That is, the number of pixels per unit length with respect to the height D of the diagnosis couch 430, the number of pixels per unit length with respect to a height at which the patient lies, and the number of pixels in a position of the patient in the y-axis direction at the diagnosis couch 430 are calculated using the fourth image, and the number of pixels described above is calculated from the second image, so that changes in the x-axis and y-axis direction in addition to the z-axis direction can be calculated. Of course, if the number of pixels per unit length in the second image and the number of pixels per unit length in the fourth image are different from each other, a change in the position of the patient in the x-axis direction of the diagnosis couch 430 has occurred. Thus, a position change of the patient in the y-axis and z-axis directions may be calculated by reflecting the change in the position of the patient in the x-axis direction.

That is, a position change of the patient in the x-axis, y-axis, and z-axis directions of the diagnosis couch 430 during previous radiation treatment and a position change of the patient in the x-axis, y-axis, and z-axis directions of the diagnosis couch 430 for current radiation treatment are calculated with reference to FIG. 2. Of course, the calculated position changes may include a change in a rotation angle in the x-axis direction, a rotation angle in the y-axis direction, and a rotation angle in the z-axis direction.

The first position change may be a position change in the x-axis or y-axis direction according to circumstances, and the second position change may be a position change in the z-axis direction, and the position changes may include rotation in addition to movement in a corresponding axis direction.

Of course, the first position change of the patient may be partially corrected or supplemented using the second position change, and similarly, the second position change of the patient may be partially corrected or supplemented using the first position change.

For example, the first position change may include a position change in the x-axis, y-axis, and z-axis directions, and the second position change may include a position change in the x-axis, y-axis, and z-axis directions. Thus, the first position change for checking a position change of the patient in the x-axis and y-axis directions may be supplemented using a position change in the x-axis and y-axis directions of the second position change, and the second position change for checking a position change of the patient in the z-axis direction may be supplemented using a position change in the z-axis direction of the first position change. Of course, the first position change and the second position change may not include only a position change in the corresponding axis direction.

Referring back to FIG. 1, if a position change of the patient in the x-axis, y-axis, and z-axis directions for current radiation treatment is calculated based on the patient position during previous radiation treatment, the patient position is automatically controlled using the calculated position changes (Operation S160).

That is, in Operation S160, the diagnosis couch 430 on which the patient lies, is moved in the x-axis, y-axis, and z-axis directions or is rotated using the calculated position changes of the patient so that the patient position is controlled to be identical to the patient position during previous radiation treatment.

Compared to previous treatment, in a current state the patient may bend, stretch further, or twist further. A plurality of markers indicated on the patient's body may look twisted in addition to being parallel/rotated/expanded/reduced between the first image and the third image. In this case, the center of the plurality of markers may be regarded as the center of the ROI and may be regarded as a criterion of position control so that Operations S160 can also be performed. In the present invention, the first camera and the second camera that capture the first image and the second image may be fixed at particular positions, but image capturing angle and position of the first camera or the second camera may be finely thrawed (dislocated) according to circumstances.

Thus, when photographing angles or positions of the first camera and the second camera that capture the patient position are changed, a position change of the patient cannot be precisely calculated. Thus, it may be determined whether the photographing angles or positions of the first camera and the second camera are identical to photographing angles or positions during previous radiation treatment, and this may be corrected.

This will be described below with reference to FIG. 3.

Figure 3:
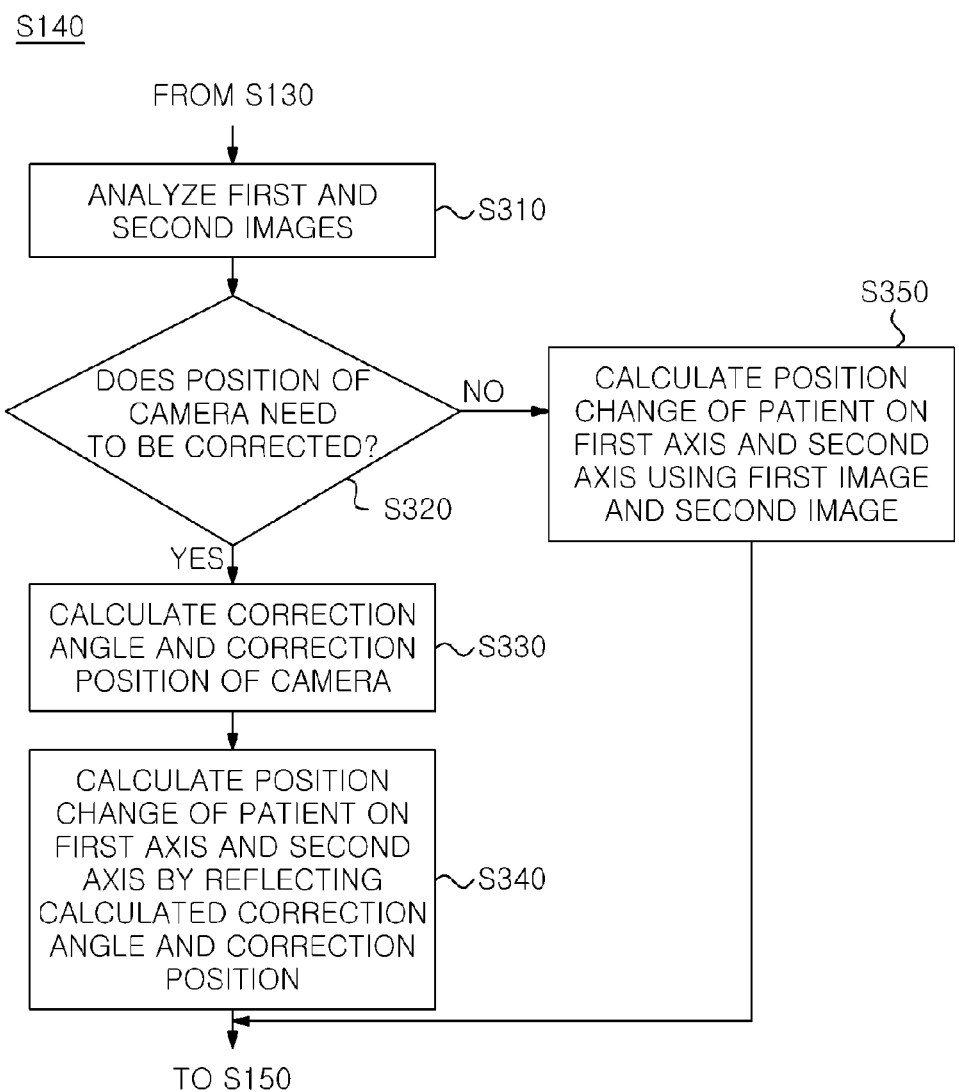
FIG. 3 is a flowchart illustrating Operation S140 illustrated in FIG. 1, in accordance with another embodiment of the present invention.

FIG. 3 is a flowchart illustrating Operation S140 illustrated in FIG. 1, in accordance with another embodiment of the present invention.

Referring to FIG. 3, Operation S140 of calculating the first position change includes analyzing the first image and the second image that are captured by the first camera and the second camera and determining whether, as a result of analyzing the first image and the second image, a position and angle of a camera need to be corrected (Operations S310 and S320).

In this case, whether to correct the camera may be performed by image processing of the diagnosis couch 430 and the patient included in the first image, and an angle direction and position of the camera may be checked through image processing. Thus, by comparing the angle direction and position of the camera with a predetermined angle direction and position of the camera, it may be determined whether the camera needs to be corrected.

That is, in Operation S320, it is determined whether a change has occurred in the angle direction and position of the camera due to an external environment or an internal problem.

As a result of determination in Operation S320, when a camera, i.e., at least one of the first camera and the second camera, needs to be corrected, an angle and position of the camera to be corrected are calculated (Operation S330).

Here, a correction angle and a correction position may be calculated by checking the angle direction and position of the camera through analysis of the first image and the second image and by comparing the checked angle direction and position with a predetermined reference angle direction and position.

If the correction angle and the correction position are calculated in Operation S330, a first position change including the first axis, the second axis, and the third axis is calculated by reflecting the calculated correction angle and correction position on the first image (Operation S340).

Of course, reflection when correction of the angle and position of the camera is performed and the position change is calculated, may be applied to the second position change in addition to the first position change.

Even when the angle of the camera is adjusted, a change in angles of the camera (the first camera or the second camera) during former treatment and in a current state may be detected based on a change in the number of pixels among the plurality of markers in each image and a change in the number of pixels between particular reference positions of the diagnosis couch 430. For example, if it is ascertained that a change in pixels between the particular reference positions of the diagnosis couch 430 has occurred between the second image and the fourth image that are captured by the second camera and the angle of the second camera has been finely thrawed, position movement in the z-axis direction derived by the second camera needs to be corrected by the change in angles of the second camera. In this case, it may be determined whether a position change has occurred even in the z-axis direction in addition to the x-y plane or where the position change has occurred, using a change in the number of pixels between the particular reference positions between the first image and the third image that are captured by the first camera. Thus, the result of calculation of the z-axis position movement of the second camera may be verified or supplemented using information extracted from the images captured by the first image.

In this way, the method of controlling the position of the radiation treatment system according to the present invention may include calculating the number of pixels per unit length by image capturing using a camera disposed at an upper portion of the diagnosis couch and a camera disposed at sides of the diagnosis couch, calculating a position change of the patient during previous radiation treatment and a position change of the patient for current radiation treatment using the calculated number of pixels per unit length, and controlling the patient position so that the diagnosis couch on which the patient lies, can be automatically moved or rotated in the x-axis, y-axis, and z-axis directions by reflecting the calculated position changes. Thus, in the method of controlling the position of the radiation treatment system according to the present invention, a radiation dose exposed to the patient can be reduced, and reliability of radiation treatment can be improved using a simple structure, and the amount of calculation can be reduced.

Furthermore, in the method of controlling the position of the radiation treatment system according to the present invention, the position changes are corrected or supplemented by reflecting the number of pixels per unit length in different images with respect to rotation or movement in a particular direction so that accuracy of position control can be improved.

In addition, according to the present invention, when an angle direction and position of the camera that captures an image has been changed, a change in angles of the camera and a position change of the camera may be calculated, and by reflecting the calculated change in angles of the camera and the calculated position change of the camera, accuracy of the first position change and the second position change of the patient position can be improved and thus, reliability of radiation treatment can be improved.

Figure 7:
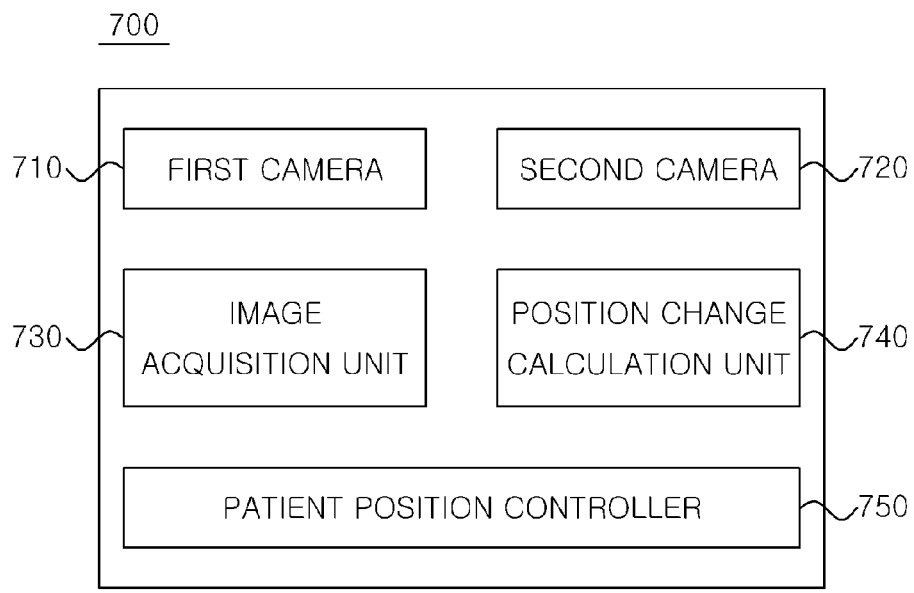
FIG. 7 is a diagram illustrating a configuration of an apparatus for controlling a position of a radiation treatment system in accordance with an embodiment of the present invention.

FIG. 7 is a diagram illustrating a configuration of an apparatus for controlling a position of a radiation treatment system in accordance with an embodiment of the present invention.

Referring to FIG. 7, an apparatus 700 for controlling a position of a radiation treatment system according to the present invention includes a first camera 710, a second camera 720, an image acquisition unit 730, a position change calculation unit 740, and a patient position controller 750.

A first camera 710 is a camera that captures an image of a patient at an upper portion of a diagnosis couch on which the patient lies during radiation treatment. The first camera 710 captures an image of the patient on a first axis and a second axis, i.e., on an x-axis and a y-axis.

A second camera 720 is a camera that captures an image of the patient at sides of the diagnosis couch on which the patient lies during radiation treatment. The second camera 720 captures an image of the patient on the second axis and the third axis, i.e., on the y-axis and a z-axis or the x-axis and the z-axis.

The image acquisition unit 730 acquires images that are captured and stored by the first camera and the second camera during previous radiation treatment, i.e., a third image and a fourth image.

In this case, the image acquisition unit 730 may acquire images of the patient during previous radiation treatment from a separate storage device or system connected to the radiation treatment system, i.e., a PACS.

The position change calculation unit 740 receives images of the patient for performing current radiation treatment, i.e., the first image captured by the first camera and the second image captured by the second camera, calculates a first position change of the patient on the first axis and the second axis using the first image and the third image, and calculates a second position change of the patient on the second axis and the third axis using the second image and the fourth image.

In this case, the position change calculation unit 740 may calculate the number of pixels per unit length in reference images and the number of pixels in the patient position on the diagnosis couch from the third image and the fourth image using the predetermined length of the diagnosis couch and may calculate the number of pixels per unit length in reference images and the number of pixels in the patient position on the diagnosis couch from the first image and the second image using the predetermined length of the diagnosis couch and then may calculate the first position change and the second position change in which a degree of position changes has occurred based on the patient position during previous radiation treatment, using the calculated number of pixels.

In addition, the position change calculation unit 740 may calculate the patient position change using the number of pixels. The position change calculation unit 740 may calculate the number of pixels based on at least one reference pattern or reference mark that is pre-set in the diagnosis couch and may calculate the patient's x-axis position, y-axis position, and z-axis position on the diagnosis couch using the number of pixels per unit length calculated based on one or more reference patterns that are pre-set on the diagnosis couch and feature points that are marked on the patient, i.e., markers indicated on eyes, nose, mouth or elsewhere on the patient's body. Furthermore, the position change calculation unit 740 may calculate the patient position on the diagnosis couch and a position change using the calculated patient position using the reference pattern of the diagnosis couch, the patient's shape, body length, and the number of pixels per unit length of lengths of a distance between body parts.

When calculating the patient's first position change by comparing the first image with the third image, the position change calculation unit 740 may correct or supplement the position change on the x-axis and the y-axis by reflecting the position change on the z-axis and may correct or supplement the position change on the y-axis and z-axis or the position change on the z-axis by reflecting the position change on the x-axis when calculating the patient's second position change by comparing the second image with the fourth image.

In addition, when calculating the patient's first position change and the patient's second position change, the position change calculation unit 740 may determine whether an angle direction and position of at least one of the first camera and the second camera through analysis of the first image and the second image needs to be corrected and then, if correction is required, may calculate a correction angle and a correction position of the camera and then may reflect the calculated correction angle and correction position on the images, thereby precisely calculating the first position change and the second position change.

The patient position controller 750 controls the patient position by moving the diagnosis couch in a first axis direction, a second axis direction, and a third axis direction and by rotating the diagnosis couch so that the patient position can be identical to the patient position during previous radiation treatment, using the first position change and the second position change that are calculated by the position change calculation unit 740.

Figure 8:
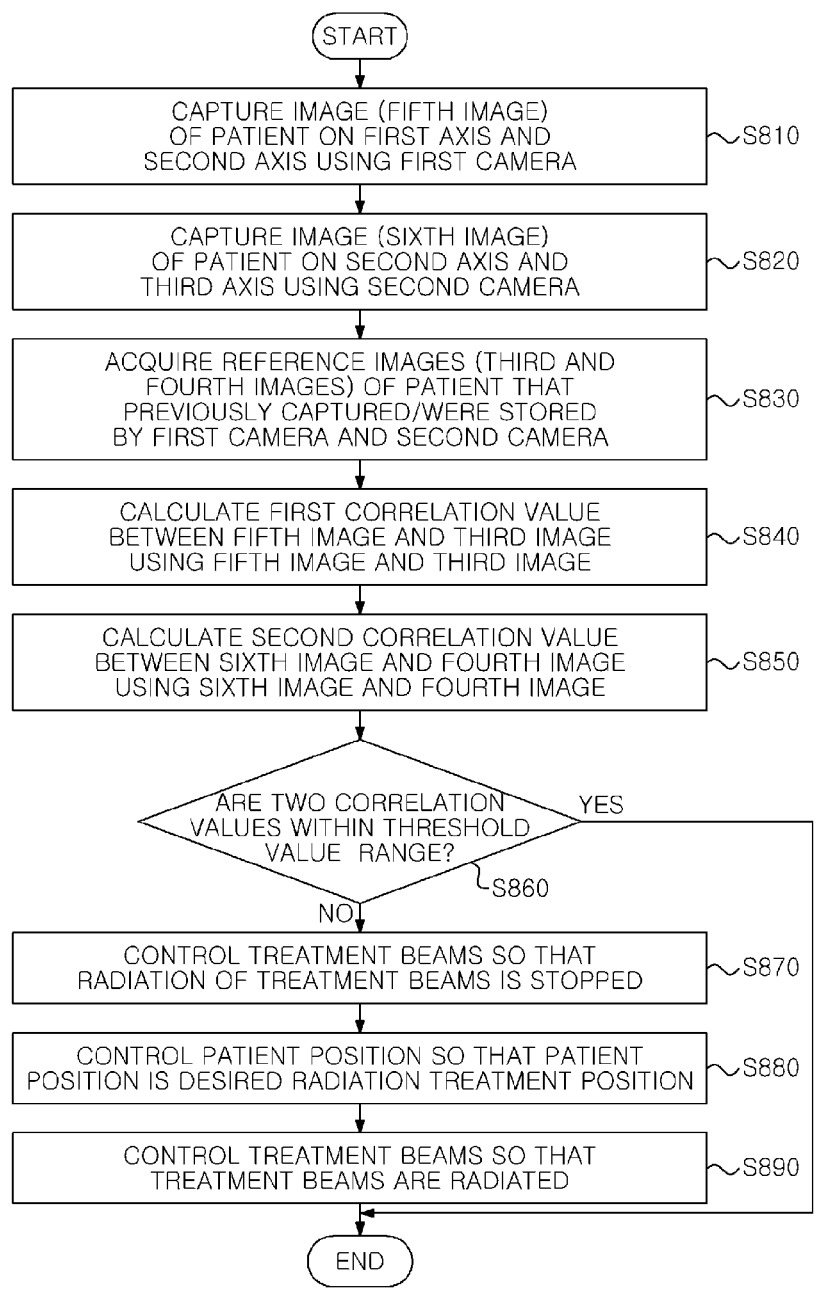
FIG. 8 is a flowchart illustrating a method of monitoring a position of a radiation treatment system in accordance with an embodiment of the present invention.

FIG. 8 is a flowchart illustrating a method of monitoring a position of a radiation treatment system in accordance with an embodiment of the present invention. The method of monitoring the position of the radiation treatment system illustrated in FIG. 8 may be executed by a processor of a computing system that may monitor the patient position or movement in the radiation treatment system and may be stored in the form of instructions to be loaded into memory connected to a processor.

The method of monitoring the position of the radiation treatment system according to the present invention relates to monitoring while radiation treatment is performed in a state in which, before radiation treatment starts being performed, the patient position on the diagnosis couch is made to be identical to the patient position during previous radiation treatment. That is, the method of monitoring the position of the radiation treatment system according to the present invention relates to monitoring the patient's movement in a state in which the patient is at a correct position so as to receive radiation treatment, in real-time.

Referring to FIG. 8, the method of monitoring the position of the radiation treatment system according to the present invention includes capturing an image of the patient on a first axis and a second axis of the diagnosis couch (hereinafter, referred to as a "fifth image") using a first camera disposed at the radiation treatment system during radiation treatment and capturing an image of the patient on the second axis and a third axis of the diagnosis couch (hereinafter, referred to as a "sixth image") using a second camera (Operations S810 and S820).

In this case, a first camera 410 may be a camera that captures an image of the patient at an upper portion of a diagnosis couch 430, and a second camera 420 may be a camera that captures an image of the patient at sides of the diagnosis couch 430, as illustrated in FIG. 4, and the first axis, the second axis, and the third axis may be an x-axis, a y-axis, and a z-axis, respectively. The first camera and the second camera may be disposed to be fixed to a gantry 440 of the radiation treatment system but may be disposed to be fixed at a different particular position instead of the gantry 440.

Thus, the fifth image captured by the first camera may be an image for mainly detecting a position change of the patient on the x-axis and the y-axis, and the sixth image captured by the second camera may be an image for mainly detecting a position change of the patient on the y-axis and the z-axis.

The fifth image and the sixth image in the present invention may be an upper image and a lateral image for monitoring the patient's movement or a position change during current radiation treatment.

If the fifth image and the sixth image are captured, the patient's reference images that previously captured by the first camera and the second camera and that were stored during previous radiation treatment, are acquired (Operation S830). In this case, the reference images are medical images including the images captured by the first camera and the second camera during previous radiation treatment, for example, during initial radiation treatment and may be the above-described third image and fourth image.

That is, the third image is an image of the patient on the x-axis and the y-axis captured by the first camera during previous radiation treatment in which radiation treatment was performed, and the fourth image is an image of the patient on the y-axis and the z-axis captured by the second camera during previous radiation treatment. The third image and the fourth image are the patient positions at which radiation treatment beams are precisely radiated onto the patient's ROI.

The third image and the fourth image may be acquired from a separate storage device or system connected to the radiation treatment system, for example, a PACS, using the patient's information. Of course, the method of monitoring the position of the radiation treatment system according to the present invention may be performed when a user's input for monitoring the patient position by a medical specialist who performs radiation treatment is received via a user interface.

If the third image and the fourth image of the patient position during previous radiation treatment are acquired in Operation S830, a correlation value between the fifth image and the third image (hereinafter, referred to as a "first correlation value") is calculated using the third image and the fifth image corresponding to the third image, and a correlation value between the sixth image and the fourth image (hereinafter, referred to as a "second correlation value") is calculated using the fourth image and the sixth image corresponding to the fourth image (Operations S840 and S850).

In this case, in Operations S840 and S850, deformation images are generated through a particular procedure and then, a correlation value between the deformation images may be calculated using the generated deformation images. A procedure of generating the deformation images for calculating the correlation value will be described below with reference to FIG. 9.

Figure 9:
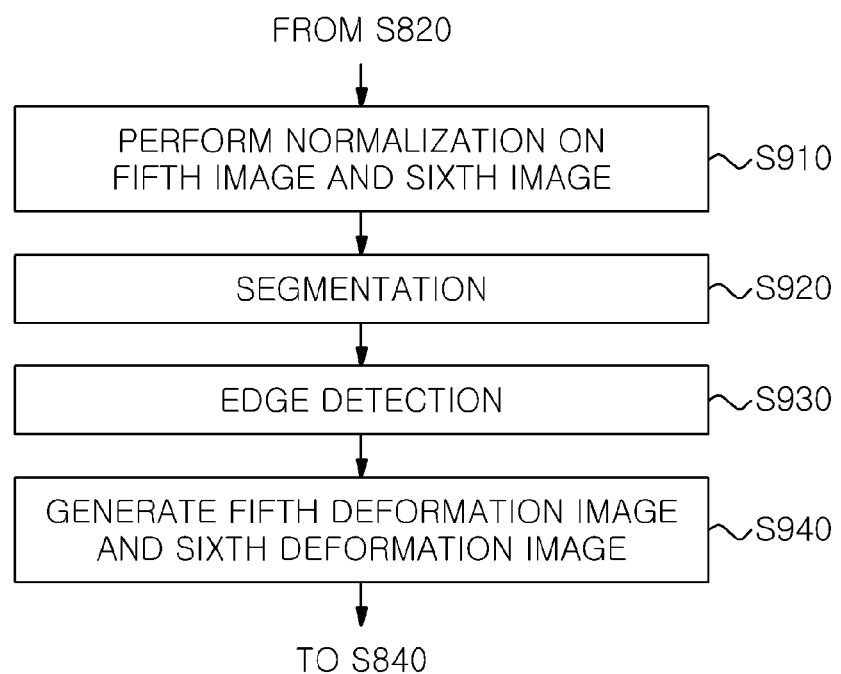
FIG. 9 is a flowchart illustrating additional operations of the method of monitoring the position of the radiation treatment system illustrated in FIG. 8.

FIG. 9 is a flowchart illustrating additional operations of the method of monitoring the position of the radiation treatment system illustrated in FIG. 8.

As illustrated in FIG. 9, if the fifth image and the sixth image are captured, the captured fifth image and the captured sixth image are received and are normalized, and the normalized images are generated as a fifth deformation image and a sixth deformation image through segmentation and edge detection (Operations S910 to S940).

Normalization, segmentation, and edge detection in FIG. 9 are sufficiently known to one of ordinary skill in the art and thus, a detailed description thereof will be omitted.

Of course, since the procedures of FIG. 9 are applied to the third image and the fourth image that were captured during previous radiation treatment, the third image and the fourth image may be generated as a third deformation image and a fourth deformation image that are generated by deforming the third image and the fourth image through normalization, segmentation, and edge detection and then, the third deformation image and the fourth deformation image may be previously stored.

Calculation of the correlation values in Operations S840 and S850 may be performed using the fifth deformation image, the sixth deformation image, the third deformation image, and the fourth deformation image, which are generated in FIG. 9. That is, a first correlation value is a correlation value obtained by comparing the fifth deformation image with the third deformation image, and a second correlation value is a correlation value obtained by comparing the sixth deformation image with the fourth deformation image.

In this case, a correlation value γ may be calculated using the following Equations 1 and 2:

$$\gamma(u, v) = \frac{\sum_{x,y} f(x, y) - \bar{f}_{u,v} \sum_{x,y} t(x-u, y-v) - \bar{t}}{\left\{ \sum_{x,y} [f(x, y) - \bar{f}_{u,v}]^2 \sum_{x,y} [t(x-u, y-v) - \bar{t}]^2 \right\}^{0.5}} \quad (1)$$

where γ(u,v) is a cross-correlation factor regarding movement distances u and v of a template image t, and (x, y) is a coordinate axis regarding a basic image f, and $\bar{f}$ is an average value of the basic image f, and $\bar{t}$ is an average value of the template image t. In the present invention, f may be the fifth deformation image or the sixth deformation image, and t may be the third deformation image or the fourth deformation image, and $\bar{f}$ may be an average value of the fifth deformation image and the sixth deformation image, and $\bar{t}$ may be an average value of the third deformation image and the fourth deformation image.

Although Equation 1 is an equation for searching for a point (u,v) in which the cross-correlation value γ is maximum, in the present invention, when images are monitored, the entire image is designated as a template image, and an object for monitoring is the entire image so that (u, v) becomes (0, 0).

Normalization of the entire image in Equation 1 may be represented by the following Equation 2.

$$\gamma = \frac{1}{n} \sum_{x,y} \frac{(f(x, y) - \overline{f})(t(x, y) - \overline{t})}{\sigma_f \sigma_t}, \quad (2)$$

where γ is a normalized cross correlation value obtained by normalizing the f-image (the fifth deformation image or the sixth deformation image) with respect to the t-image (the third deformation image of the fourth deformation image), and n is the number of pixels, and f is the fifth deformation image or the sixth deformation image, and t is the third deformation image or the fourth deformation image, and $\overline{f}$ is an average value of the fifth deformation image and the sixth deformation image, and $\overline{t}$ is an average value of the third deformation image and the fourth deformation image, and $\sigma_f$ is a standard deviation with respect to the f-image, and $\sigma_t$ is a standard deviation with respect to the t-image.

Referring back to FIG. 8, if the first correlation value and the second correlation value are calculated in Operations S840 and S850, it is determined whether two calculated correlation values (the first correlation value and the second correlation value) are within a predetermined threshold value range (Operation S860).

That is, in Operation S860, it is determined whether all of two correlation values are within the predetermined threshold value range.

As a result of determination in Operation S860, if it is determined that two correlation values are out of the threshold value range, it is determined that the patient has moved thus affecting radiation treatment, and then treatment beams is controlled so that radiation of treatment beams are stopped (Operation S870).

The diagnosis couch is moved or rotated so that the patient position is a desired treatment position at which radiation treatment is to be performed, by calculating a position change caused by the patient's movement, thereby controlling the patient position (Operation S880).

In this case, controlling of the patient position may include calculating a third position change of the patient on the first axis and the second axis using the fifth image and the third image, calculating a fourth position change of the patient on the second axis and the third axis using the sixth image and the fourth image, and controlling the diagnosis couch so that the patient position is the desired treatment position, using the calculated third position change and the calculated fourth position change. The number of pixels per unit length in a corresponding image is calculated using a predetermined length of the diagnosis couch so that the patient position changes can be calculated.

The patient position changes may include a change in a rotation angle in the x-axis direction, a rotation angle in the y-axis direction, and a rotation angle in the z-axis direction, and the third position change may be a position change in the x-axis or y-axis direction according to circumstances, and the position changes may include rotation in addition to movement in a corresponding axis direction.

The position changes for controlling the patient position are calculated based on markers indicated on the patient's body or a particular reference position of an ISO center and a previously-checked diagnosis couch. According to the present invention, all of a change in the patient positions and changes in the patient's poses can be calculated.

Of course, in Operation S880, the diagnosis couch on which the patient lies, is moved so that a ROI of radiation treatment can be correctly positioned on a path of radioactive rays and thus radiation treatment in a current state can achieve a predetermined objective, by calculating a difference between the position and the pose of the patient during previous radiation treatment and the current position and the current pose of the patient, thereby controlling the patient position.

The patient may have moved in x-axis and y-axis directions from the diagnosis couch or may be lying obliquely. Alternatively, the patient's pose may be slightly twisted compared to his or her position in a previous treatment. A position change of the patient in an x-y plane and rotation on the x-y plane may be extracted by comparing the fifth image with the third image using a plurality of markers indicated on the patient's body. Also, when the patient's pose is a supine pose, a prone pose, or a lateral pose, a difference between the supine pose, the prone pose, or the lateral pose and a twisted pose of the patient compared to former treatment may also be detected.

Also, by analyzing a change in pixels between particular reference positions of the diagnosis couch, even though positions of the diagnosis couch are the same, it may be checked whether the position or pose of the patient has changed or whether a change in the orientation of the diagnosis couch itself has occurred.

For example, in Operation S880, the number of pixels in a predetermined length of the diagnosis couch, for example, a width or length of the diagnosis couch, and the number of pixels in the patient position are calculated from the third image, and the number of pixels in the width or length of the diagnosis couch and the number of pixels in the patient position are calculated from the fifth image, and a position change of the patient is calculated using the calculated number of pixels, and the diagnosis couch on which the patient lies, is moved in the x-axis, y-axis, and z-axis directions or rotated using the calculated position change so that the patient position is controlled to be identical to the patient position during previous radiation treatment.

In this case, positions of the patient in the x-axis and y-axis directions of the diagnosis couch may be calculated based on an end of the diagnosis couch or based on at least one reference pattern or a reference mark that is pre-set in the diagnosis couch. Of course, the patient position in the x-axis and y-axis directions on the diagnosis couch may be calculated using the number of pixels per unit length that is calculated based on at least one reference pattern that is pre-set in the diagnosis couch and feature points that are marked on the patient, i.e., markers indicated on the eyes, nose, mouth or elsewhere on the patient, and the x-axis position and the y-axis position of the patient on the diagnosis couch may be calculated using the reference pattern, the patient's shape, body length, and the number of pixels per unit length of lengths of a distance between body parts.

Of course, if the patient position on the diagnosis couch has changed, the number of pixels per unit length is the same, and if movement has occurred on the diagnosis couch, the number of pixels per unit length may be changed. Thus, the patient position may be controlled in consideration of this change, and position change information in a different image is reflected on calculation of the patient position so that a position change in a corresponding image can be corrected or supplemented.

Of course, as a result of Operation S860, stopping of radiation of radiation treatment beams when two correlation values are out of the threshold value range may be informed to a medical specialist using an alarm.

Also, according to the present invention, images of a patient who receives radiation treatment, are captured using two fixed cameras in real-time so that the patient's breathing period data can be generated by analyzing the patient's images captured in real-time and the patient's breathing period data generated in this way can be provided as a graph.

During previous treatment and in a current state, the patient may bend, stretch further, or twist further. A plurality of markers indicated on the patient's body may look twisted in addition to being parallel/rotated/expanded/reduced between the fifth image and the third image. In this case, the center of the plurality of markets may be regarded as the center of the ROI and may be regarded as a reference of position control so that Operation S890 can be performed. In the present invention, the first camera and the second camera that capture the fifth image and the sixth image may be fixed at particular positions, but image capturing angle and position of the first camera or the second camera may be finely thrawed (dislocated) according to circumstances.

Thus, when the photographing angle or position of the first camera and the second camera that capture the patient position is changed, the patient position cannot be precisely monitored. Thus, it may be determined whether photographing angles or positions of the first camera and the second camera are identical to photographing angles or positions during previous radiation treatment, and this may be corrected so that the patient position can be monitored.

This will be described below with reference to FIG. 10.

Figure 10:
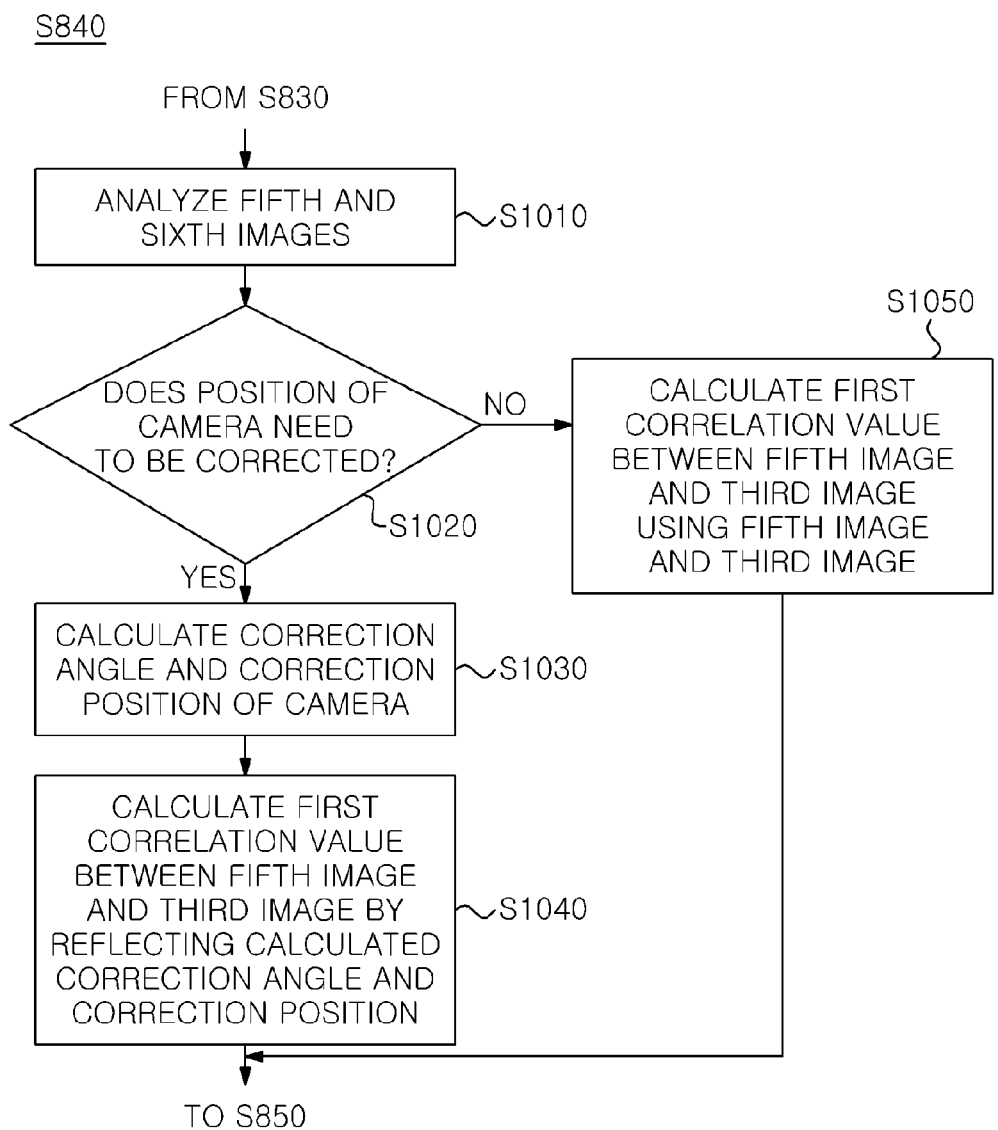
FIG. 10 is a flowchart illustrating Operation S840 illustrated in FIG. 8 in accordance with another embodiment of the present invention.

FIG. 10 is a flowchart illustrating Operation S840 illustrated in FIG. 8 in accordance with another embodiment of the present invention.

Referring to FIG. 10, Operation S840 of calculating the first correlation value includes analyzing the fifth image and the sixth image that were captured by the first camera and the second camera and determining whether, as a result of analyzing the fifth image and the sixth image, the position and angle of the camera need to be corrected (Operation S1010 and S1020).

In this case, whether to correct the camera may be performed by image processing of the diagnosis couch and the patient included in the fifth image, and an angle direction and position of the camera may be checked through image processing. Thus, by comparing the angle direction and position of the camera with a predetermined angle direction and position of the camera, it may be determined whether the camera needs to be corrected.

That is, in Operation S1020, it is determined whether a change in the angle direction and position of the camera has occurred due to an external environment or an internal problem.

As a result of determination in Operation S1020, when a camera, i.e., at least one of the first camera and the second camera needs to be corrected, an angle and a position of the camera to be corrected are calculated (Operation S1030).

Here, a correction angle and a correction position may be calculated by checking the angle direction and position of the camera through analysis of the fifth image and the sixth image and by comparing the checked angle direction and position with a predetermined reference angle direction and position.

If the correction angle and the correction position are calculated in Operation S1030, a first correlation value between the fifth image and the third image is calculated by reflecting the calculated correction angle and correction position (Operation S1040).

In this case, in Operation S1040, the first correlation value may be generated by a correlation between the fifth image and the third image after reflecting the calculated correction angle and correction position of the camera on the fifth image, or the first correlation value may also be generated by reflecting the calculated correction angle and correction position when the first correlation value is calculated.

On the other hand, if, as a result of determination in Operation S1020, position correction of the camera is not required, the first correlation value between the fifth image and the third image is calculated using only the captured fifth image and third image, as described above (S1050).

Of course, reflection when correction of the angle and position of the camera is performed and the position change is calculated may be applied to a second correction value in addition to the first correlation value.

Even when the angle of the camera is adjusted, a change in angles of the camera (the first camera or the second camera) during former treatment and in a current state may be detected based on a change in the number of pixels among the plurality of markers in each image and a change in the number of pixels between particular reference positions of the diagnosis couch. For example, if it is ascertained that a change in pixels between the particular reference positions of the diagnosis couch has occurred between the sixth image and the fourth image that are captured by the second camera and the angle of the second camera has been finely thrawed, position movement in the z-axis direction derived by the second camera needs to be corrected by the change in angles of the second camera. In this case, it may be determined whether a position change has occurred even in the z-axis direction in addition to the x-y plane or where the position change has occurred, using a change in the number of pixels between the particular reference positions between the fifth image and the third image that are captured by the first camera. Thus, the result of calculation of the z-axis position movement of the second camera may be verified or supplemented using information extracted from the images captured by the first image.

In order to determine whether the angle and position of the camera need to be corrected, a reference image of the patient's optimum position may be provided, and it may be determined whether the angle and position of the camera need to be corrected, and a correction angle and a correction position may also be calculated by comparing the reference image with an image captured by the camera.

In this way, the method of monitoring the position of the radiation treatment system according to the present invention may include calculating a correlation value between images captured using a camera disposed at an upper portion of the diagnosis couch and a camera disposed at sides of the diagnosis couch during radiation treatment and images (reference images) captured during previous radiation treatment and monitoring whether the patient's movement occurs, using the calculated correlation value, so that, even when the patient has moved, radiation treatment beams is controlled so that radiation treatment beams can be radiated onto a desired ROI and thus, even when the patient has moved, a normal part can be prevented from being exposed to treatment beams.

Also, in the method of monitoring the position of the radiation treatment system according to the present invention, even when angle directions and angle positions of the first camera and the second camera are changed due to an external environment, the changed angle and position are reflected on calculation of the correlation value so that the patient's movement can be precisely monitored and reliability of radiation treatment can also be improved.

Figure 11:
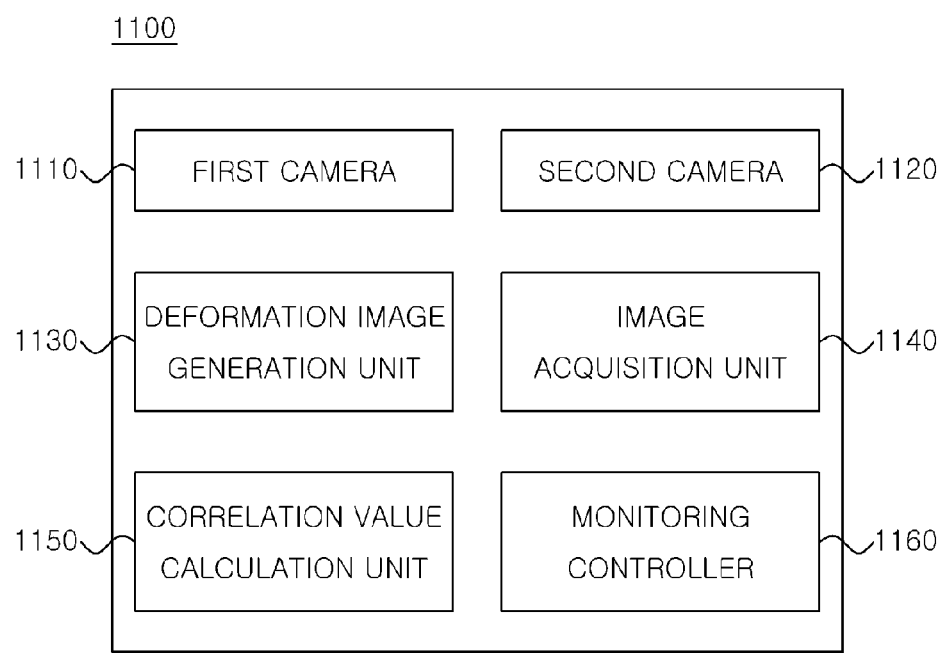
FIG. 11 is a diagram illustrating a configuration of an apparatus for monitoring a position of a radiation treatment system in accordance with an embodiment of the present invention.

FIG. 11 is a diagram illustrating a configuration of an apparatus for monitoring a position of a radiation treatment system in accordance with an embodiment of the present invention.

Referring to FIG. 11, an apparatus 1100 for monitoring a position of a radiation treatment system according to the present invention includes a first camera 1110, a second camera 1120, a deformation image generation unit 1130, an image acquisition unit 1140, a correlation value calculation unit 1150, and a monitoring controller 1160. The deformation image generation unit 1130, the image acquisition unit 1140, the correlation value calculation unit 1150, and the monitoring controller 1160 may be configured by a processor of a computing system that may monitor the patient position or movement.

The first camera 1110 is a camera that captures images of the patient at an upper portion of a diagnosis couch on which the patient lies during radiation treatment, and captures images of the patient on a first axis and a second axis, i.e., on an x-axis and a y-axis.

The second camera 1120 is a camera that captures images of the patient at sides of the diagnosis couch on which the patient lies during radiation treatment, and captures images of the patient on the second axis and a third axis, i.e., on the y-axis and a z-axis or on the x-axis and the z-axis.

The deformation image generation unit 1130 generates the images that are captured by the first camera 1110 and the second camera 1120, as deformation images in which the images are deformed, through normalization, segmentation, and edge detection.

That is, the deformation image generation unit 1130 generates a third deformation image and a fourth deformation image through normalization, segmentation, and edge detection performed on a third image and a fourth image that are captured during previous radiation treatment and generates a fifth deformation image and a sixth deformation image through normalization, segmentation, and edge detection performed on the fifth image and the sixth image that are captured during current radiation treatment.

The image acquisition unit 1140 acquires images that are captured and stored by the first camera and the second camera during previous radiation treatment, i.e., the third image and the fourth image.

In this case, the image acquisition unit 1140 may acquire a fifth deformation image and a sixth deformation image in which the fifth image and the sixth image are deformed. The image acquisition unit 1140 may acquire images of the patient during previous radiation treatment from a separate storage device or system connected to the radiation treatment system, for example, a PACS.

The correlation value calculation unit 1150 receives the fifth image and the sixth image that are captured by the first camera and the second camera during current radiation treatment, calculates a first correlation value between the fifth image and the third image by comparing the fifth image with the third image, and calculates a second correlation value between the sixth image and the fourth image by comparing the sixth image with the fourth image.

In this case, the correlation value calculation unit 1150 may receive the fifth deformation image and the sixth deformation image from the deformation image generation unit 1130, may calculate the first correlation value by comparing the fifth deformation image with the third deformation image, and may calculate the second correlation value by comparing the sixth deformation image with the fourth deformation image.

That is, the correlation value calculation unit 1150 determines whether an angle and a position of at least one of the first camera and the second camera need to be corrected, by comparing the fifth image and the sixth image with reference images corresponding to the fifth image and the sixth image, for example, the third image and the fourth image, and if correction is required, calculates a correction value of the angle and the position of at least one of the first camera and the second camera, and calculates the first correlation value and the second correlation value by reflecting the calculated correction value.

Furthermore, when the correlation value calculation unit 1150 calculates a correlation value for determining the patient's movement, the correlation value calculation unit 1150 determines whether an angle direction and an angle position of at least one of the first camera and the second camera need to be corrected through analysis of the fifth image and the sixth image, and if correction is required, the correlation value calculation unit 1150 calculates a correction angle and a correction position of the camera and then reflects the calculated correction angle and correction position so as to calculate the correlation value, thereby precisely calculating the first correlation value and the second correlation value.

The monitoring controller 1160 determines whether the first correlation value and the second correlation value are within a predetermined threshold value range, and if the first correlation value and the second correlation value are out of the threshold value range, the monitoring controller 1160 determines that the patient position is out of a desired radiation treatment position, and controls treatment beams so that radiation of the treatment beams performed stopped.

Furthermore, the monitoring controller 1160 controls the diagnosis couch on which the patient lies, so that the patient position is the desired radiation treatment position, and if the patient position is the desired radiation treatment position, the monitoring controller 1160 controls the radiation beams to be radiated at the radiation treatment position.

In this case, the monitoring controller 1160 calculates the patient's third position change on the first axis and the second axis using the fifth image and the third image, calculates the patient's fourth position change on the second axis and the third axis using the sixth image and the fourth image and controls the diagnosis couch so that the patient position is the desired radiation position using the calculated third position change and fourth position change. The monitoring controller 1160 calculates the number of pixels per unit length of a corresponding image using a predetermined length of the diagnosis couch, thereby calculating the patient position change.

Thus, the monitoring controller 1160 calculates a position change including a degree of the patient's movement and rotation in the x-axis, y-axis, and z-axis directions and causes the diagnosis couch to be moved or rotated in the x-axis, y-axis, and z-axis directions using the calculated position change, thereby controlling the position so that the patient's is in the desired treatment position.

The method of controlling the position of the radiation treatment system or the method of monitoring the position of the radiation treatment system in accordance with the embodiments of the present invention may be implemented in the form of program instructions that are executable by various types of computer means, and may be recorded in a computer-readable storage medium. The computer-readable storage medium may include program instructions, data files, and data structures either independently or in combination. The program instructions stored in the medium may be designed and configured especially for the present invention or may be known to and usable by those skilled in the art of computer software. Examples of the computer-readable storage medium may include a magnetic medium, such as a hard disk, a floppy disk, or magnetic tape, an optical medium, such as CD-ROM or a DVD, a magneto-optical medium, such as a floptical disk, and a hardware apparatus, such as ROM, RAM, or flash memory which is especially configured to store and execute the program instructions. Examples of the program instructions include not only such machine language code that is created by a compiler, but also such high-level language code that is executable by a computer using an interpreter or the like. The hardware apparatus can be configured to function as one or more software modules so as to perform the operation of the present invention, and vice versa.

As described above, according to the present invention, the position of a patient can be automatically controlled as a reference position by comparing images of the patient's reference position with images of the patient position during current radiation treatment using two fixed cameras so that a radiation dose exposed to the patient can be reduced.

In addition, according to the present invention, the position of the patient is automatically controlled at the diagnosis couch using the number of pixels in the patient's reference position and the number of pixels in the patient position during current radiation treatment so that the amount of calculation for correction of the patient position can be reduced.

In addition, according to the present invention, a photographing position of the camera is reflected using images of a reference photographing position of the camera so that reliability of controlling the patient position can be improved and reliability of radiation treatment can also be improved.

In detail, according to the present invention, an angle or position of the camera is corrected using the diagnosis couch, and a change in the patient positions is corrected or supplemented by reflecting the corrected angle or position of the camera so that reliability of controlling the patient position during radiation treatment can be improved.

According to the present invention, there is provided a method of controlling a position of a radiation treatment system, whereby the reference position of the diagnosis couch and a position change of markers indicated on the patient's body are sensed even using two cameras having a comparatively simple configuration so that the present invention can respond to fine twisting of the angle of the camera and a fine change in the patient position and the patient's pose.

In addition, according to the present invention, by comparing images of the patient's reference position with images of the patient position during current radiation treatment using two fixed cameras, even when the moves during treatment, his or her position is controlled through patient monitoring so that radiation treatment beams can be radiated onto a desired ROI. Thus, even when the moves, a normal part can be prevented from being exposed to treatment beams.

That is, according to the present invention, the patient position is monitored using a correlation value of images of the patient's reference position involved in radiation treatment and a correlation value of the patient's images captured during radiation treatment so that the patient position can be controlled in such a way that treatment beams can be radiated onto the ROI, such as a tumor.

In addition, according to the present invention, the photographing position of the camera is reflected using images of a reference photographing position of the camera so that reliability of monitoring the patient position can be improved and thus reliability of radiation treatment can also be improved.

In detail, according to the present invention, an angle or position of the camera is corrected by analyzing images captured during radiation treatment, and monitoring of the patient position is performed by reflecting the corrected angle or position of the camera so that reliability of monitoring the patient position can be improved.

According to the present invention, there is provided a method of monitoring a position of a radiation treatment system, whereby the reference position of the diagnosis couch and positions of markers indicated on the patient's body or a position of an ISO center are sensed even using two cameras having a comparatively simple configuration so that fine twisting of the angle of the camera and a fine change in the patient position and the patient's pose can be monitored.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of controlling a position of a radiation treatment system, comprising:
   capturing, by a processor, a first image of a patient on a first axis and a second axis using a first camera and capturing a second image of the patient on the second axis and a third axis using a second camera;
   acquiring, by the processor, a third image of the patient captured using the first camera and a fourth image of the patient captured using the second camera during previous radiation treatment;
   calculating, by the processor, a first position change of the patient on the first axis and the second axis using the first image and the third image and calculating a second position change of the patient on the second axis and the third axis using the second image and the fourth image;
   calculating, by the processor, a third position change of the patient along the third axis using a difference between a first number of reference pixels and a second number of reference pixels, wherein the first number of reference pixels is defined as a number of pixels between first reference points in the first image and the second number of reference pixels is defined as a number of pixels between the first reference points in the third image;
   verifying by the processor, the second position change of the patient on the third axis using the third position change; and
   controlling, by the processor, a position of the patient using the first position change and the second position change so that the position of the patient is identical to a position of the patient during previous radiation treatment.

2. The method of claim 1, wherein the calculating of the first position change of the patient and the second position change of the patient comprises calculating the first position change and the second position change using at least one selected from the group consisting of at least one reference pattern that is previously formed on a diagnosis couch on which the patient lies, at least one feature point that is marked on the patient, and the patient's shape.

3. The method of claim 1, wherein the calculating of the first position change of the patient and the second position change of the patient comprises calculating a first number of pixels on a length of a diagnosis couch on which the patient lies, and a second number of pixels on the position of the patient within the diagnosis couch from the third image and the fourth image, calculating a third number of pixels on the length of the diagnosis couch and a fourth number of pixels on the position of the patient within the diagnosis couch from the first image and the second image, and calculating the first position change and the second position change using the calculated first to fourth numbers of pixels.

4. The method of claim 1, wherein the controlling of the position of the patient comprises controlling the position of the patient by moving or rotating a diagnosis couch on which the patient lies, in directions of the first axis, the second axis, and the third axis using the first position change and the second position change.

5. An apparatus for controlling a position of a radiation treatment system, comprising:
a first camera that captures an image of a patient on a first axis and a second axis at a diagnosis couch;
a second camera that captures an image of the patient on the second axis and a third axis; and
a processor configured to:
acquire a first image and a second image of the diagnosis couch and the patient that were captured and stored by the first camera and the second camera during previous radiation treatment;
receive a third image and a fourth image that are captured by the first camera and the second camera for current radiation treatment, calculate a first position change of the patient on the first axis and the second axis using the first image and the third image and calculate a second position change of the patient on the second axis and the third axis using the second image and the fourth image;
calculate a third position change of the patient along the third axis using a difference between a first number of reference pixels and a second number of reference pixels, wherein the first points of reference pixels is defined as a number of pixels between first reference points in the first image and the second number of reference pixels is defined as a number of pixels between the first reference points in the third image;
verify the second position change of the patient on the third axis using the third position change ; and
control a position of the patient using the first position change and the second position change so that the position of the patient is identical to a position of the patient during previous radiation treatment.

6. The apparatus of claim 5, wherein the processor is further configured to calculate the first position change and the second position change using at least one selected from the group consisting of at least one reference pattern that is previously formed on the diagnosis couch on which the patient lies, at least one feature point that is marked on the patient, and the patient's shape.

7. The apparatus of claim 5, wherein the processor is further configured to calculate a first number of pixels on a length of the diagnosis couch on which the patient lies, and a second number of pixels on the position of the patient within the diagnosis couch from the first image and the second image, calculates a third number of pixels on the length of the diagnosis couch and a fourth number of pixels on the position of the patient within the diagnosis couch from the third image and the fourth image, and calculates the first position change and the second position change using the calculated first to fourth numbers of pixels.

8. The apparatus of claim 5, wherein the processor is further configured to control the position of the patient by moving or rotating the diagnosis couch on which the patient lies, in directions of the first axis, the second axis, and the third axis using the first position change and the second position change.

9. A method of monitoring a position of a radiation treatment system, comprising:
capturing, by a processor, a first image of a patient on a first axis and a second axis using a first camera and capturing a second image of the patient on the second axis and a third axis using a second camera during radiation treatment;
acquiring, by the processor, a third image of the patient captured using the first camera and a fourth image of the patient captured using the second camera during previous radiation treatment;
calculating, by the processor, a first correlation value between the first image and the third image by comparing the first image with the third image and calculating a second correlation value between the second image and the fourth image by comparing the second image with the fourth image;
calculating, by the processor, information about thraw and a position change of the patient along the third axis based on a difference between a first number of reference pixels and a second number of reference pixels, wherein the first number of reference pixels is defined as a number of pixels between first reference in the first image and the second number of reference pixels is defined as a number of pixels between the first reference point in the third image;
verifying, by the processor, the second correlation value using the information about the thraw and the position change of the patient along the third axis; and
determining, by the processor, whether the first correlation value and the second correlation value are within a predetermined threshold value range, and if it is determined that the first correlation value and the second correlation value are out of the predetermined threshold value range, determining that the position of the patient is out of a desired radiation treatment position, and controlling treatment beams so that radiation of the treatment beams is stopped.

10. The method of claim 9, further comprising:
controlling, by the processor, a diagnosis couch on which the patient lies, so that the position of the patient is the desired radiation treatment position; and
if the position of the patient is the desired radiation treatment position, controlling, by the processor, the treatment beams so that the treatment beams are radiated.

11. The method of claim 9, wherein the acquiring of the third image of the patient and the fourth image of the patient comprises acquiring a third deformation image and a fourth deformation image that are generated by deforming the third image and the fourth image through normalization, segmentation, and edge detection, and
the calculating of the first correlation value and the second correlation value comprises, after acquiring a first deformation image and a second deformation image that are generated by deforming the first image and the second image through normalization, segmentation, and edge detection, calculating the first correlation value by comparing the first deformation image with the third deformation image and calculating the second correlation value by comparing the second deformation image with the fourth deformation image.

12. The method of claim 9, further comprising:
determining, by the processor, whether correction of an angle and position of at least one of the first camera and the second camera is required by comparing the first image and the second image with reference images corresponding to the first image and the second image; and
as a result of determination, if correction is required, calculating, by the processor, a correction value of the angle and position of at least one of the first camera and the second camera,
wherein the calculating of the first correlation value and the second correlation value comprises calculating the first correlation value and the second correlation value using the calculated correction value of the angle and position of the at least one of the first camera and the second camera.

13. An apparatus for monitoring a position of a radiation treatment system, comprising:
a first camera that captures an image of a patient on a first axis and a second axis at a diagnosis couch;
a second camera that captures an image of the patient on the second axis and a third axis; and
a processor configured to:
acquire a first image and a second image of the diagnosis couch and the patient that were previously captured and stored by the first camera and the second camera during previous radiation treatment;
receive a third image and a fourth image that are captured by the first camera and the second camera during current radiation treatment, calculate a first correlation value between the first image and the third image by comparing the first image with the third image and calculates a second correlation value between the second image and the fourth image by comparing the second image with the fourth image;
calculate information about thraw and a change of the patient along the third axis based on a difference between a first number of reference pixels and a second number of reference pixels, wherein the first number of reference pixels is defined as a number of pixels between first reference points in the first image and the second number of reference pixels is defined as a number of pixels between the first reference points in the third image;
verify the second correlation value using the information about the thraw and the position change of the patient along the third axis; and
determine whether the first correlation value and the second correlation value are within a predetermined threshold value range, and if it is determined that the first correlation value and the second correlation value are out of the predetermined threshold value range, determine that the position of the patient is out of a desired radiation treatment position, and control treatment beams so that radiation of the treatment beams is stopped.

14. The apparatus of claim 13, wherein the processor is further configured to control the diagnosis couch on which the patient lies, so that the position of the patient is the desired radiation treatment position, and if the position of the patient is the desired radiation treatment position, control the treatment beams so that the treatment beams are radiated.

15. The apparatus of claim 13, wherein the processor is further configured to:
acquire a first deformation image and a second deformation image that are generated by deforming the first image and the second image through normalization, segmentation, and edge detection;
acquire a third deformation image and a fourth deformation image that are generated by deforming the third image and the fourth image through normalization, segmentation, and edge detection; and
calculate the first correlation value by comparing the first deformation image with the third deformation image and calculate the second correlation value by comparing the second deformation image with the fourth deformation image.

16. The apparatus of claim 13, wherein the processor is further configured to determine whether correction of an angle and position of at least one of the first camera and the second camera is required by comparing the first image and the second image with reference images corresponding to the first image and the second image, and as a result of determination, if correction is required, calculate a correction value of the angle and position of at least one of the first camera and the second camera, and calculate the first correlation value and the second correlation value using the calculated correction value of the angle and position of the at least one the first camera and the second camera.

* * * * *